United States Patent [19]

Tsuno et al.

[11] Patent Number: 5,808,133

[45] Date of Patent: Sep. 15, 1998

[54] ALICYCLIC BIFUNCTIONAL COMPOUNDS AND PROCESSES FOR THEIR PREPARATION

[75] Inventors: Takaharu Tsuno; Hideki Kobayashi, both of Tsukuba, Japan

[73] Assignee: Arakawa Chemical Industries Ltd., Osaka, Japan

[21] Appl. No.: 796,344

[22] Filed: Feb. 7, 1997

Related U.S. Application Data

[62] Division of Ser. No. 522,711, Sep. 1, 1995, Pat. No. 5,670,696.

[30] Foreign Application Priority Data

Sep. 2, 1994 [JP] Japan .................................. 6-234171
Sep. 2, 1994 [JP] Japan .................................. 6-234172

[51] Int. Cl.⁶ .................................................. C07C 69/74
[52] U.S. Cl. ........................ 560/117; 562/498; 568/817
[58] Field of Search ............................ 560/117; 562/498; 568/817

[56] References Cited

U.S. PATENT DOCUMENTS 4,797,488  1/1989  Stack et al. .

5,214,125  5/1993  Mitani et al. .

FOREIGN PATENT DOCUMENTS 60-203630  10/1985  Japan .

OTHER PUBLICATIONS

Journal of the American Chemical Society, vol. 96, pp. 7237–7248, Glen A. Russell, et al. (1974).

*Primary Examiner*—Michael L. Shippen
*Attorney, Agent, or Firm*—Knobbe, Matens, Olson & Bear, LLP

[57] ABSTRACT

The invention provides an alicyclic bifunctional compound represented by the formula

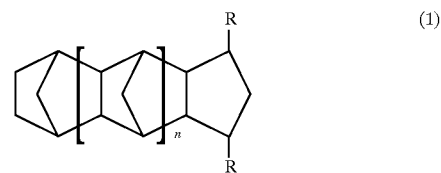

(1)

wherein R is a carboxyl group, a lower alkoxycarbonyl group or a hydroxymethyl group and n is 0 or 1.

15 Claims, No Drawings

ALICYCLIC BIFUNCTIONAL COMPOUNDS AND PROCESSES FOR THEIR PREPARATION

RELATED APPLICATION

The present application is a divisional application of application Ser. No. 08/522,711, filed Sep. 1, 1995, now U.S. Pat. No. 5,670,696.

The present invention relates to novel alicyclic compounds and processes for preparing the compounds. The invention more particularly concerns with alicyclic bifunctional compounds useful as materials for polyesters, polycarbonates, etc. and with processes for their preparation.

Polyesters prepared from monomers having an alicyclic skeleton such as alicyclic dicarboxylic acids or alicyclic diols have been known as excellent in physical and chemical properties, e.g. transparency, heat resistance, chemical resistance, dimensional stability, etc. Such properties due to the alicyclic skeleton allow the polyesters to be used as polymer components for optical materials, structural materials or the like, such as optical disks, optical cards, or liquid crystal display components.

There are known various alicyclic bifunctional compounds useful as monomers for polyesters having an alicyclic skeleton. For example, Japanese Unexamined Patent Publications Nos. 200,830/1991, 5,026/1993 and 17,560/1993, etc. disclose alicyclic diol compounds such as bicyclo[2. 2. 1]heptane-2,3-dimethanol, tetracyclo[4. 4. 0. $1^{2,5}$. $1^{7,10}$]-3,4-dimethanol, hexacyclo[6. 6. 1. $1^{3,6}$. $1^{10,13}$. $0^{2,7}$. $0^{9,14}$]heptadecane-4,5-dimethanol, etc., alicyclic dicarboxylic acids such as bicyclo[2. 2. 1]heptane-2,3-dicarboxylic acid, tetracyclo[4. 4. 0. $1^{2,5}$. $1^{7,10}$]-3,4-dicarboxylic acid, hexacyclo[6. 6. 1. $1^{3,6}$. $1^{10,13}$. $0^{2,7}$. $0^{9,14}$]heptadecane-4,5-dicarboxylic acid, etc. and diesters thereof.

However, said known alicyclic bifunctional compounds have drawbacks. These alicyclic compounds, in any case of the diol compounds or the dicarboxylic acid compounds, have two functional groups on vicinal carbons of their alicyclic skeleton. Such neighboring relationship of the two functional groups obviously causes steric hindrance, thus making it difficult to produce a polymer having a higher molecular weight due to the low reactivity of the monomer. Consequently, the obtained polyesters contain considerable amounts of low molecular weight condensates and show a wide distribution of molecular weight, posing a problem that the polyester fails to exhibit its inherent properties, such as heat resistance, moisture resistance and chemical resistance, to a full extent although excellent in transparency and mechanical properties.

An object of the present invention is to provide novel alicyclic bifunctional compounds free of said drawbacks of known alicyclic bifunctional compounds, and processes for preparing the novel compounds.

Other objects and features of the invention will become more apparent from the following description.

The alicyclic bifunctional compounds of the present invention are represented by the formula

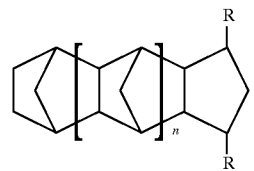
(1)

wherein R is a carboxyl group, a lower alkoxycarbonyl group or a hydroxymethyl group and n is 0 or 1.

The foregoing compounds of the invention include alicyclic cis-dicarboxylic acid represented by the formula

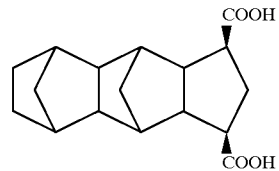
(2)

and alicyclic trans-dicarboxylic acid represented by the formula

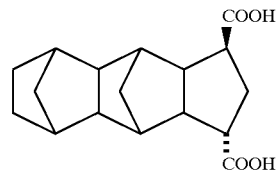
(3)

The compounds of the present invention further include alicyclic cis-dicarboxylic diesters represented by the formula

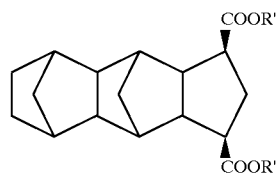
(4)

wherein R' is a lower alkyl group having 1 to 4 carbon atoms, and alicyclic trans-dicarboxylic diesters represented by the formula

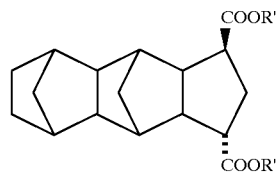
(5)

wherein R' is as defined above.

The compounds of the present invention also include alicyclic cis-diols represented by the formula

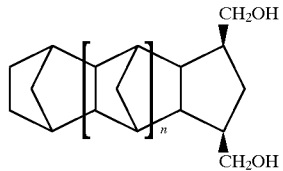
(6)

wherein n is as defined above, and alicyclic trans-diols represented by the formula

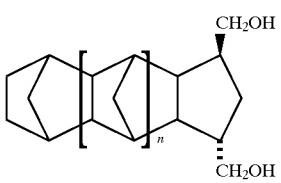

wherein n is as defined above.

Examples of the lower alkyl group of 1 to 4 carbon atoms represented by R' in the invention are methyl, ethyl, n-propyl, iso-propyl, n-butyl, sec-butyl, tert-butyl, etc. Examples of the lower alkoxycarbonyl group represented by R include carboxyl groups esterified with said lower alkyl group.

The alicyclic bifunctional compounds of the formula (1) of the present invention can be prepared from a starting compound, i.e. an alicyclic monoolefin represented by the formula

wherein n is as defined above, for example, according to the following reaction scheme.

Reaction scheme

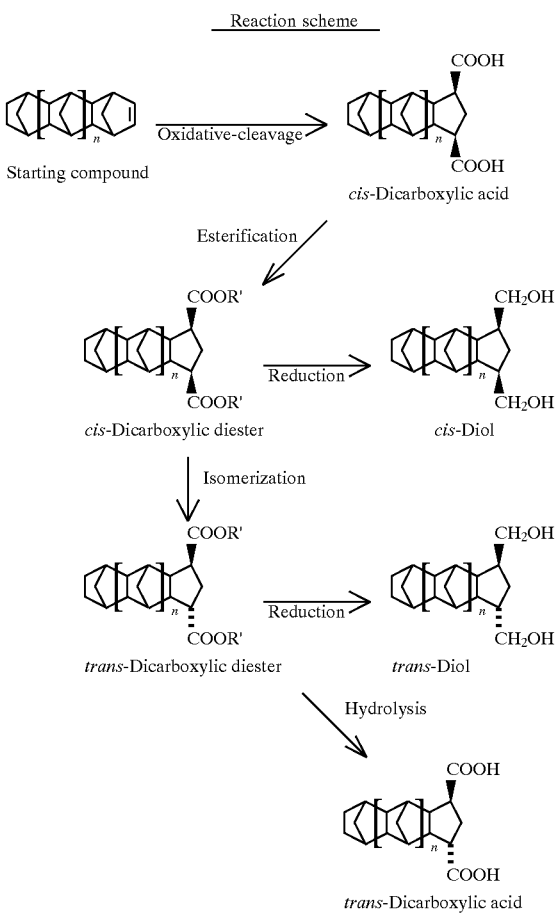

In the foregoing reaction scheme, n and R' are as defined above.

The alicyclic cis-dicarboxylic acids of the formula (2) can be prepared by subjecting the double bond of alicyclic monoolefin of the formula (8) (wherein n is 1) to oxidative-cleavage reaction.

The alicyclic trans-dicarboxylic acids of the formula (3) can be prepared by isomerizing the alicyclic cis-dicarboxylic diester of the formula (4) into a trans form, and hydrolyzing the trans form.

The alicyclic cis-dicarboxylic diesters of the formula (4) can be prepared by subjecting the double bond of alicyclic monoolefin of the formula (8) (wherein n is 1) to oxidative-cleavage reaction to give a cis-dicarboxylic acid, and esterifying the cis-dicarboxylic acid.

The alicyclic trans-dicarboxylic diesters of the formula (5) can be prepared by isomerizing the alicyclic cis-dicarboxylic diester of the formula (4) into a trans form.

The alicyclic cis-diols of the formula (6) can be prepared by subjecting the double bond of alicyclic monoolefin of the formula (8) to oxidative-cleavage reaction to give a cis-dicarboxylic acid, esterifying the cis-dicarboxylic acid into a cis-dicarboxylic diester, and reducing the diester.

The alicyclic trans-diols of the formula (7) can be prepared by subjecting the double bond of alicyclic monoolefin of the formula (8) to oxidative-cleavage reaction to give a cis-dicarboxylic acid, esterifying the cis-dicarboxylic acid into a cis-dicarboxylic diester, isomerizing the diester into a trans form and reducing the trans form.

The alicyclic monoolefins of the formula (8) which are used as the starting compound in the present invention are known compounds, and the monoolefins can be prepared by known processes. Such monoolefins can most typically be prepared by a Diels-Alder reaction of cyclopentadiene or dicyclopentadiene as a diene with ethylene or norbornene as a dienophile. For example, the reaction of cyclopentadiene with norbornene usually gives various Diels-Alder adducts, e.g. a 1:1 adduct, 2:1 adduct or 3:1 adduct of the diene and the dienophile. Product selectivity of these adducts depends on the reaction conditions such as the molar ratio of the diene and dienophile, reaction temperature, reaction time, etc. Thus, by the choice of proper reaction conditions, the reaction would produce the desired adduct: tetracyclo[4. 4. 0. $1^{2,5}$. $1^{7,10}$]-3-dodecene (n is 0 in the formula (8); 1:1 adduct) or hexacyclo[6. 6. 1. $1^{3,6}$. $1^{10,13}$. $0^{2,7}$. $0^{9,14}$]-4-heptadecene (n is 1 in the formula (8); 2:1 adduct). The obtained alicyclic monoolefin can be easily isolated by vacuum distillation or the like.

Conventional methods per se known can be used for the oxidative-cleavage reaction of the double bond of alicyclic monoolefin of the formula (8) to give an alicyclic cis-dicarboxylic acid.

Various processes are known for preparing a dicarboxylic acid by one-step oxidative cleavage of carbon-carbon double bond in the presence of an oxidizing agent. For example, there are known a process involving oxidation under alkaline to neutral conditions using a permanganate (J. Chem. Soc., Perkin. Trans. 1,806 (1973)), a process using a bichromate (org. Synth., vol.3, p.449 (1955)), a process using a periodate in the presence of a ruthenium metal catalyst (J. Org. Chem., vol.46, p.19 (1981)), a process using nitric acid (Japanese Unexamined Patent Publication No.190,945/1984), a process using ozone (J. Am. Chem. Soc., vol.81, p.4,273 (1959)), etc. These known processes for oxidative-cleavage reactions can be used as such in preparing the alicyclic cis-dicarboxylic acids of the invention from the alicyclic monoolefins of the formula (8).

The inventor of the present invention carried out extensive research on said oxidative-cleavage reactions and found the following. The contemplated alicyclic cis-dicarboxylic acid is produced in low yields when using a permanganate, bichromate or nitric acid as an oxidizing agent, whereas the contemplated acid can be produced in high yields when using a periodate or ozone as an oxidizing agent. However, from a viewpoint of commercial manufacture, the use of periodate or ozone entails the disadvantages of necessitating cumbersome reaction work-up, requiring expensive reagents, etc.

The inventor carried out further investigations on the foregoing oxidative-cleavage reactions and discovered that when the oxidative-cleavage reaction is effected under acidic conditions using a permanganate as an oxidizing agent, the contemplated alicyclic cis-dicarboxylic acid can be produced in a high yield. While conventional oxidative-cleavage reactions have been performed under alkaline to neutral conditions, the inventor's proposed oxidative cleavage reaction is carried out under acidic conditions under which the oxidizing ability of a permanganate is enhanced. The proposed oxidative-cleavage reaction will be described below.

Potassium permanganate is desirable among permanganates useful as an oxidizing agent. The amount of the permanganate used is at least 1 mole equivalent, preferably 2 to 4 mole equivalents, per mole of the alicyclic monoolefin of the formula (8).

Usually sulfuric acid, hydrochloric acid, acetic acid, nitric acid and like inorganic or organic acids can be used to bring the reaction system to acidic conditions. Among these acids, sulfuric acid, hydrochloric acid and like inorganic acids are desirable since these acids lead to the decrease in the amount of decomposition products formed as by-products, and they are inexpensive. These acids may be used as diluted with water, namely in the form of an aqueous solution or may be used as such without dilution. The amount of the acid used is about 0.2 to about 3 mole equivalents, preferably about 0.4 to about 2 mole equivalents, per mole of the alicyclic monoolefin of the formula (8). If less than 0.2 mole equivalent of the acid is used, the contemplated product is produced in a lower yield, whereas if more than 3 mole equivalents is used, decomposition products are formed as by-products due to the acid. Hence the use of the acid in an amount outside said range is undesirable.

Solvents useful in the oxidative-cleavage reaction are not specifically limited insofar as they are inert to the reaction. Useful solvents include, for example, water, acetone; tetrahydrofuran, dioxane and like ethers; benzene, toluene, xylene and like aromatic hydrocarbons; hexane, heptane and like aliphatic hydrocarbons; methyl chloride, dichloromethane, chloroform and like halogenated hydrocarbons; etc. Among these solvents, it is desirable, in view of the solubility of the alicyclic monoolefin of the formula (8) and permanganate, to use a mixture of water and an organic solvent in an amount of at least one part by weight per part by weight of the alicyclic monoolefin of the formula (8). More preferably, a water-acetone mixture in a ratio by weight of 1:9–9:1 is used in an amount of at least 3 parts by weight per part by weight of the alicyclic monoolefin of the formula (8).

In the aforesaid oxidative-cleavage reaction, the alicyclic monoolefin of the formula (8), permanganate and acid may be charged in a lump together with the solvent and reacted. Or the reaction may proceed while these components are continuously or intermittently charged for the reaction. Other orders of charging are possible. For example, only the permanganate may be dissolved or suspended in the solvent first, and the alicyclic monoolefin of the formula (8) and acid may be continuously or intermittently added to the reaction system. Or only the alicyclic monoolefin of the formula (8) may be dissolved or suspended in the solvent first, and the permanganate and acid may be continuously or intermittently added to the reaction system. Reversely, the alicyclic monoolefin of the formula (8) and acid may be charged first, and the permanganate may be continuously or intermittently added to the reaction system, or the permanganate and acid may be charged first, and the alicyclic monoolefin of the formula (8) may be continuously or intermittently added to the reaction system. As a further alternative, the alicyclic monoolefin of the formula (8) and permanganate may be supplied first, and the acid may be continuously or intermittently added to the reaction system.

The temperature for the oxidative-cleavage reaction is in the range of about $-20°$ to about $100°$ C., preferably $0°$ to about $40°$ C. The reaction time is variable depending on the molar ratio of the alicyclic monoolefin of the formula (8) to a permanganate and on the reaction temperature, but is usually in the range of about 2 to about 24 hours.

The alicyclic cis-dicarboxylic acid prepared by said oxidative-cleavage reaction is esterified into an alicyclic cis-dicarboxylic diester.

The esterification can be conducted in the conventional manner. For example, the esterification is easily carried out by one of the following procedures: (i) using a lower alcohol in the presence of an acid catalyst, (ii) converting the cis-dicarboxylic acid to a dicarboxylic acid salt, followed by esterification with a lower alkyl halide, (iii) converting the cis-dicarboxylic acid to an acid halide, followed by esterification with a lower alcohol, and (iv) using a lower alkyl diazo compound such as diazomethane.

Among the above procedures, the procedure using a lower alcohol in the presence of an acid catalyst is preferred from a commercial viewpoint. Stated more specifically, this procedure comprises esterifying the alicyclic cis-dicarboxylic acid with a monohydric alcohol having 1 to 4 carbon atoms in the presence of an acid catalyst such as p-toluenesulfonic acid, sulfuric acid or the like. Examples of the monohydric alcohol are methanol, ethanol, n-propanol, iso-propanol, n-butanol, sec-butanol, tert-butanol, etc. It is suitable to conduct the esterification in the monohydric alcohol. In this case, a preferred amount of monohydric alcohol used is at least 3 times the weight of the alicyclic cis-dicarboxylic acid.

The alicyclic cis-dicarboxylic diester obtained by the esterification reaction is reduced to an alicyclic cis-diol compound.

The reduction can be easily conducted in the conventional manner by reducing the lower alkoxycarbonyl group to a hydroxymethyl group. A recommendable reduction is effected, for example, through catalytic hydrogenation, or using a metallic hydride compound such as $NaBH_4$, $LiAlH_4$, etc., or using a metal such as Li, Na, etc.

Among said procedures, the catalytic hydrogenation is preferred in view of commercial manufacture.

The catalytic hydrogenation can be performed by reducing the alicyclic cis-dicarboxylic diester with hydrogen gas in the presence of a hydrogenation catalyst. Useful hydrogenation catalysts include, for example, copper-chromite, palladium-tin, rhodium-tin, ruthenium-tin and palladium-zinc catalysts. Among them, a copper-chromite catalyst is preferred.

It is known to use copper-chromite as a catalyst in catalytic hydrogenation for reduction from a diester compound to the corresponding diol compound (Org. React., vol.8, pp.1–27 (1954)). Various grades of copper-chromite catalysts are commercially used. Commercially available copper-chromite catalysts can be used as such or in combination with a metallic reduction catalyst such as tin, rhodium, molybdenum, palladium, iron, etc. which serves as a promoter.

The amount of the hydrogenation catalyst used is about 0.01 to about 15% by weight based on the alicyclic cis-dicarboxylic diester. A less amount of the catalyst used prolongs the reduction, whereas its excess amount tends to cause a side reaction. Hence the use of catalyst in an amount outside said range is undesirable from a viewpoint of commercial manufacture.

The catalytic hydrogenation is usually conducted in a solvent. Useful solvents are not specifically limited insofar as they are inert to the reaction. Useful solvents are, for example, benzene, toluene, xylene, cumene and like aromatic hydrocarbons, hexane, heptane, octane and like aliphatic hydrocarbons, alcohol solvents, ether solvents, etc. The amount of the solvent used is about 0.1 to about 50 parts by weight per part by weight of the alicyclic cis-dicarboxylic diester.

An ambient or higher pressure is employed as a hydrogen pressure in the catalytic hydrogenation. A suitable hydrogen pressure is usually 10 kg/cm$^2$ or higher. When a copper-chromite catalyst is used, the hydrogen pressure is preferably 100 kg/cm$^2$ or higher, more preferably 200 kg/cm$^2$ or higher. A lower pressure than said range defers the progress of catalytic hydrogenation and is disadvantageous from a viewpoint of commercial manufacture. The reaction is accelerated with an increase of temperature, and this is advantageous from a viewpoint of commercial manufacture insofar as a side reaction is not involved at an increased temperature. A suitable reaction temperature is in the range of about 100° to about 300° C., preferably about 170° to about 300° C. The reactor is not critical insofar as it is a pressure reactor conventionally used for catalytic hydrogenation.

The alicyclic cis-dicarboxylic diester obtained by the foregoing esterification is isomerized to bring the two ester groups into a trans configuration relation with each other, whereby an alicyclic trans-dicarboxylic diester is produced.

The isomerization reaction is carried out preferably in a manner to cause a metal alkoxide as a catalyst to act on the alicyclic cis-dicarboxylic diester.

In this case, an isomerization occurs with ease and in a high yield due to the catalytic effect of a metal alkoxide used. Generally a carbonyl compound having hydrogen in the α-position of carbonyl group is known to have a keto-enol type equilibrium in the presence of a basic catalyst. The above-mentioned isomerization reaction was devised by the application of this characteristic. A metal alkoxide has not been conventionally used for cis-trans isomerization of a substituent diester group on a polycyclic aliphatic compound. Such isomerization was discovered for the first time by the present inventor.

The present inventor conducted experiments using, as a catalyst for isomerization reaction, alkali metal hydroxides such as sodium hydroxide, potassium hydroxide, etc., alkali metal amides such as lithium diisopropyl amide (LDA), etc. However, their use resulted in a lower isomerization yield than when said alkoxide catalysts were used, or in a side reaction. That is, good results were not obtained.

Examples of metal alkoxides which can be used as a catalyst in said isomerization reaction are methoxide, ethoxide, n-propoxide, iso-propoxide, n-butoxide, sec-butoxide, tert-butoxide and pentoxide of alkali metals such as lithium, sodium, potassium and the like. These metal alkoxides may be prepared separately for this purpose or may be prepared in the same system for the isomerization reaction. In the case of preparing a metal alkoxide in the reaction system, for instance an alcohol is reacted with an alkali metal or alkali metal hydride in the solvent used in the isomerization reaction or in a solvent inert to the reaction, and the resulting solution is used as such in the reaction. These metal alkoxides may be used singly or in mixture with each other. The amount of the catalyst used is not specifically limited, but preferably in the range of about 0.05 mole to about 0.5 mole equivalent, per mole of the alicyclic cis-dicarboxylic diester. If the amount of the catalyst is less than 0.05 mole equivalent, an isomerization would not occur or would proceed at an extremely low rate. Hence it is unpractical. On the other hand, the amount of more than 0.5 mole equivalent would entail a risk of various side reactions concurring. Hence it is undesirable.

While said isomerization is feasible in the absence of a solvent, a suitable solvent is preferably used. Solvents for use herein are not critical insofar as they are capable of partially or completely dissolving the alicyclic trans-dicarboxylic diester and they are inert to the reaction. Examples of such solvents are organic solvents including ethers such as diethyl ether, tetrahydrofuran, dioxane, etc.; aromatic hydrocarbons such as benzene, toluene, xylene, etc.; aliphatic hydrocarbons such as hexane, heptane, etc.; alcohols such as methanol, ethanol, etc. Preferred are aprotic organic solvents such as tetrahydrofuran, dioxane and like ethers. These solvents which are commercially available can be used as such to achieve fully satisfactory results, and those purified by distillation are more desirable.

The temperature for the isomerization reaction is in the range of about −50° to about 100° C., preferably about −10° to 50° C. A reaction time of 5 hours or less is sufficient in most cases because the isomerization quickly proceeds under the above-specified conditions.

The alicyclic trans-dicarboxylic diester obtained by said isomerization reaction can be converted to an alicyclic trans-diol by being reduced under the same conditions as in the reduction of the alicyclic cis-dicarboxylic diester.

An alicyclic trans-dicarboxylic acid can be produced by hydrolyzing in the conventional manner the alicyclic trans-dicarboxylic diester obtained by said isomerization reaction. The hydrolysis can be easily conducted in the presence of either an acid catalyst or an alkali catalyst commonly employed. Useful acid catalysts include, for example, hydrochloric acid, sulfuric acid, etc. Useful alkali catalysts are, for example, sodium hydroxide, potassium hydroxide, etc.

In this way, the alicyclic bifunctional compounds of the formula (1) according to the invention can be prepared.

According to the present invention, there are provided novel alicyclic bifunctional compounds and processes for preparing the compounds. Such alicyclic bifunctional compounds of the invention are useful as materials for polyesters, polycarbonates, etc. Since two functional groups in the alicyclic compounds of the invention are not on vicinal carbons of the alicyclic skeleton, the compound of the invention, when used as a material for a polyester having an alicyclic skeleton, would be unlikely to cause steric hindrance and can be easily made into a polymer having a higher molecular weight. Because a cis form or a trans form alone among the compounds of the formula (1) can be selectively produced according to the invention, only the alicyclic skeleton of the cis or trans form can be introduced into a polymer such as a polyester. As a matter of course, the novel compounds of the invention can also be used as a mixture of cis and trans forms.

The present invention will be described below in more detail with reference to the following Examples but is not limited thereto.

EXAMPLE 1

Preparation of pentacyclo[6. 5. 1. 1$^{3,6}$. 0$^{2,7}$. 0$^{9,13}$] penta-decane-cis-10, 12-dicarboxylic acid (alicyclic cis-dicarboxylic acid of the formula (2))

Acetone (2 l), 700 ml of water, 35.5 ml (0.67 mole) of sulfuric acid, and 302 g (1.91 moles) of potassium permanganate were charged into a 5 l separable flask equipped with a stirrer, condenser, thermometer and dropping funnel. A 144 g (0.64 mole) quantity of hexacyclo[6. 6. 1. $1^{3,6}$. $1^{10,13}$. $0^{2,7}$. $0^{9,14}$]-4-heptadecene-(alicyclic monoolefin of the formula (8) wherein n is 1) was added dropwise with stirring at 10° to 15° C. over a period of 1 hour, followed by 24 hours of reaction at room temperature. After removal of manganese dioxide formed from the reaction mixture by filtration, the filtrate was concentrated under reduced pressure, giving 151 g of crude crystals of alicyclic cis-dicarboxylic acid of the formula (2). The crystals were recrystallized from a solvent mixture of 140 ml of dimethyl sulfoxide (DMSO) and 115 ml of water, giving 125 g of white crystals having a melting point (decomposition) of 256° to 258° C. in a yield of 67 mole % (hereinafter simply indicated by %) based on the starting material, i.e. hexacyclohep-tadecene. It was confirmed by $^1$H-NMR, $^{13}$C-NMR, IR and elementary analysis that the crystals were identical with the contemplated alicyclic cis-dicarboxylic acid. The spectrum data are as follows.

$^1$H-NMR (DMSO-$d_6$): 0.89–0.93 (m, 4H), 1.37–1.42 (m, 3H), 1.57 (s, 2H), 1.66 (dt, 1H), 1.72 (d, 1H), 2.03 (s, 4H), 2.16 (q, 1H), 2.56 (d, 2H), 2.88–2.98 (m, 2H), 12.05 (s, 2H) (ppm); $^{13}$C-NMR (DMSO-$d_6$): 174.05, 49.65, 47.02, 44.06, 43.73, 38.70, 35.63, 34.79, 32.57, 30.98 (ppm); IR (KBr): 2959, 1719, 1687, 1265, 1202 (cm$^{-1}$);Elementary analysis ($C_{17}H_{22}O_4$);Calcd.: C, 70.32; H, 7.64; Found: C, 70.25; H, 7.54

EXAMPLE 2

The same procedure as in Example 1 was carried out except that the flask was charged with acetone, water, and potassium permanganate, first and then sulfuric acid and hexacyclo[6. 6. 1. $1^{3,6}$. $1^{10,13}$. $0^{2,7}$. $0^{9,14}$]-4-heptadecene were added dropwise to the reaction system through different dropping funnels over a period of 1 hour. After recrystallization, 130 g of white crystals were obtained (yield 70%). It was confirmed by $^1$H-NMR, $^{13}$C-NMR, IR and elementary analysis that the crystals were identical with the alicyclic cis-dicarboxylic acid of the formula (2) prepared in Example 1.

EXAMPLE 3

The same procedure as in Example 1 was conducted except that the amount of sulfuric acid was changed to 18 ml (0.34 mole). After recrystallization, 122 g of white crystals were obtained (yield 66%). It was confirmed by $^1$H-NMR, $^{13}$C-NMR, IR and elementary analysis that the crystals were identical with the alicyclic cis-dicarboxylic acid of the formula (2) prepared in Example 1.

EXAMPLE 4

Preparation of pentacyclo[6. 5. 1. $1^{3,6}$. $0^{2,7}$. $0^{9,13}$]penta-decane-cis-10, 12-dimethyl dicarboxylate (alicyclic cis-dicarboxylic diester of the formula (4) wherein R' is a methyl group)

The alicyclic cis-dicarboxylic acid of the formula (2) prepared in Example 1 (375 g, 1.30 moles), 14.5 g (76 mmoles) of p-toluenesulfonic acid and 3.5 l of methanol were charged into a 5 l separable flask equipped with a stirrer, thermometer and condenser. An esterification reaction was performed at a methanol-refluxing temperature for 12 hours. After completion of the reaction, the methanol was distilled off under reduced pressure, giving 415 g of a pale yellow powder. The powder was recrystallized from methanol, whereby 381 g of white crystals having a melting point of 142° to 143° C. was obtained in a yield of 92%. It was confirmed by $^1$H-NMR, $^{13}$C-NMR, IR and elementary analysis that the crystals were identical with the contemplated alicyclic cis-dimethyl dicarboxylate. The spectrum data are as follows.

$^1$H-NMR (CDCl$_3$): 0.95 (dd, 2H), 0.97 (d, 1H), 1.03 (d, 1H), 1.42–1.50 (m, 2H), 1.57 (bs, 1H), 1.61 (bs, 2H), 1.68 (d, 1H), 1.88 (dt, 1H), 1.96 (s, 2H), 2.13 (s, 2H), 2.52 (q, 1H), 2.69 (d, 2H), 2.95–3.08 (m, 2H), 3.72 (s, 6H) (ppm); $^{13}$C-NMR (CDCl$_3$): 173.38, 51.46, 50.18, 47.70, 44.89, 44.33, 39.07, 36.05, 35.16, 32.71, 31.35 (ppm); IR (KBr): 2943, 1735, 1726, 1439, 1381, 1245, 1189, 1150 (cm$^{-1}$); Elementary analysis ($C_9H_{26}O_4$); Calcd.: C, 71.67; H, 8.23 ; Found: C, 71.55; H, 8.33

EXAMPLE 5

Preparation of pentacyclo[6. 5. 1. $1^{3,6}$ $0^{2,7}$. $0^{9,13}$] penta-decane-trans-10, 12-dimethyl dicarboxylate (alicyclic trans-dicarboxylic diester of the formula (5) wherein R' is a methyl group)

The alicyclic cis-dimethyl dicarboxylate (274 g, 0.86 mole) prepared in Example 4, 1 l of tetrahydrofuran and 19.3 g (0.17 mole) of potassium tert-butoxide were charged into a 2 l separable flask equipped with a stirrer, thermometer, dropping funnel and nitrogen gas inlet tube. The mixture was stirred at 0° C. for 2 hours. With the addition of 50 ml of water, the reaction mixture was quenched and was concentrated to about 300 ml under reduced pressure. The concentrate was subjected to fractional extraction with 1 l of water and 1 of ethyl acetate. The obtained organic layer was concentrated under reduced pressure, giving 268 g of pale yellow solids. The solids were recrystallized from hexane, giving 255 g of white crystals having a melting point of 52° to 53° C. (yield 93%). It was confirmed by $^1$H-NMR, $^{13}$C-NMR, IR and elementary analysis that the crystals were identical with the contemplated alicyclic trans-dimethyl dicarboxylate. The spectrum data are as follows.

$^1$H-NMR (CDCl$_3$): 0.92 (d, 1H), 0.98 (dd, 2H), 1.10 (d, 1H), 1.32 (d, 1H), 1.45 (d, 2H), 1.55 (d, 1H), 1.68 (s, 2H), 1.94 (t, 1H), 2.04–2.12 (m, 1H), 2.14 (s, 2H), 2.23 (s, 2H), 2.23–2.35 (m, 2H), 2.49 (d, 2H), 3.69 (s, 6H) (ppm); $^{13}$C-NMR (CDCl$_3$): 175.16, 51.68, 49.18, 48.96, 46.85, 45.25, 36.27, 35.93, 35.06, 33.90, 31.27 (ppm); IR (KBr): 2950, 1736, 1726, 1438, 1367, 1251, 1194, 1143 (cm$^{-1}$); Elementary analysis ($C_{19}H_{26}O_4$); Calcd.: C, 71.67; H, 8.23 ; Found: C, 71.64; H, 8.35

EXAMPLE 6

The same procedure as in Example 5 was conducted except that the amount of potassium tert-butoxide was changed to 9.7 g (0.09 mole) in Example 5. After recrystallization, 248 g of white crystals were obtained (yield 91%). It was confirmed by $^1$H-NMR, $^{13}$C-NMR, IR and elementary analysis that the crystals were identical with the alicyclic trans-dimethyl dicarboxylate prepared in Example 5.

EXAMPLE 7

The same procedure as in Example 5 was conducted except that 9.18 g (0.17 mole) of sodium methoxide was used in place of the potassium tert-butoxide used as a catalyst in Example 5. After recrystallization, 248 g of white crystals were obtained (yield 91%). It was confirmed by $^1$H-NMR, $^{13}$C-NMR, IR and elementary analysis that the crystals were identical with the alicyclic trans-dimethyl dicarboxylate prepared in Example 5.

EXAMPLE 8

Preparation of pentacyclo[6. 5. 1. 1$^{3,6}$. 0$^{2,7}$. 0$^{9,13}$] penta-decane-trans-10, 12-dicarboxylic acid (alicyclic trans-dicarboxylic acid of the formula (3))

The alicyclic trans-dimethyl dicarboxylate (51 g, 0.16 mole) prepared in Example 5, 20 g of sodium hydroxide and 500 ml of water were charged into a 1 l 4-necked flask equipped with a stirrer, thermometer and condenser. The mixture was thoroughly stirred at 105° C. for 2 hours. After completion of the reaction, concentrated hydrochloric acid was added until a pH of 1 was reached. The precipitated white crystals were filtered, washed with water and dried, giving 46 g of white crystals having a melting point (decomposition) of 240° to 242.5° C. (yield 99%). It was confirmed by $^1$H-NMR, $^{13}$C-NMR, IR and elementary analysis that the crystals were identical with the contemplated alicyclic trans-dicarboxylic acid of the formula (3). The spectrum data are as follows. $^1$H-NMR (CDCl$_3$): 0.87–1.01 (m, 4H), 1.37–1.51 (m, 4H), 1.62 (q, 1H), 1.64 (bs, 2H), 1.93 (quin, 1H), 2.05 (s, 2H), 2.12 (s, 2H), 2.17–2.26 (m, 2H), 2.32 (d, 2H), 12.08 (s, 2H) (ppm); $^{13}$C-NMR (CDCl$_3$): 175.87, 48.69, 48.51, 46.40, 44.83, 35.89, 35.64, 34.64, 33.77, 30.88 (ppm); IR (KBr): 2944, 1728, 1700, 1278, 1205 (cm$^{-1}$); Elementary analysis (Cl$_7$H$_{22}$O$_4$); Calcd.: C, 70.32; H, 7.64 ; Found: C, 70.25; H, 7.80

EXAMPLE 9

(i) Preparation of tricyclo[5. 2. 1. 0$^{2,6}$]decane-cis-3, 5-dimethyl dicarboxylate A 5 l separable flask equipped with a stirrer, condenser, thermometer and dropping funnel was charged with 2 l of acetone, 700 ml of water, 35.5 ml (0.67 mole) of sulfuric acid and 302 g (1.91 moles) of potassium permanganate. Added dropwise was 103 g (0.64 mole) of tetracyclo[4. 4. 0. 1$^{2,5}$. 1$^{7,10}$]-3-dodecene (alicyclic monoolefin of the formula (8) wherein n is 0) with stirring at 10° to 15° C. over 1 hour. The mixture was further reacted at room temperature for 24 hours. After removal of manganese dioxide formed from the reaction mixture, the filtrate was concentrated under reduced pressure, giving 99 g of crude crystals of alicyclic cis-dicarboxylic acid. The crystals were recrystallized from a solvent mixture of 110 ml of dimethyl sulfoxide (DMSO) and 90 ml of water, giving 85 g of white crystals having a melting point of 250° to 255° C.

A 5 l separable flask equipped with a stirrer, thermometer and condenser was charged with 85 g (0.38 mole) of the above-obtained alicyclic cis-dicarboxylic acid, 4.3 g (22 mmole) of p-toluenesulfonic acid and 850 ml of methanol. The mixture was subjected to esterification reaction at a methanol-refluxing temperature for 12 hours. After completion of the reaction, the methanol was distilled off under reduced pressure, giving 95 g of a pale yellow powder. The powder was recrystallized from methanol, giving 86 g of white crystals having a melting point of 98° to 100° C. (yield 53%). It was confirmed by $^1$H-NMR, $^{13}$C-NMR, IR and elementary analysis that the crystals were identical with the contemplated tricyclo[5. 2. 1. 0$^{2,6}$]decane-cis-3, 5-dimethyl dicarboxylate.

(ii) Preparation of tricyclo[5. 2. 1. 0$^{2,6}$]decane-cis-3,5-dimethanol (alicyclic cis-diol of the formula (6) wherein n is 0)

A 300 ml autoclave equipped with an electromagnetic stirrer was charged with 30 g (0.12 mole) of the tricyclo[5. 2. 1. 0$^{2,6}$]decane-cis-3,5-dimethyl dicarboxylate prepared above in (i), 150 ml of dioxane and 0.5 g of a copper-chromite catalyst. The system was fully replaced with hydrogen gas and was further supplied with hydrogen gas to a pressure of 200 kg/cm$^2$. Reduction was effected with stirring at 200° C. for 20 hours. After completion of the reaction, the system was cooled to 60° C. or lower, the catalyst was filtered off and the dioxane was distilled off under reduced pressure. The obtained pale yellow powder was recrystallized from a methanol-ethyl acetate solvent mixture, producing 19.8 g of white crystals with a melting point of 115° to 117° C. (yield 85%). It was confirmed by $^1$H-NMR, $^{13}$C-NMR, IR and elementary analysis that the crystals were identical with the contemplated tricyclo[5. 2. 1. 0$^{2,6}$]decane-cis-3,5-dimethanol. The spectrum data are as follows.

$^1$H-NMR (CDCl$_3$): 0.96 (q, 1H), 1.04 (dt, 1H), 1.09 (dd, 2H), 1.21 (dt, 1H), 1.36–1.48 (m, 4H), 1.82 (dt, 1H), 2.11 (dt, 2H), 2.23 (bs, 2H), 2.22–2.36 (m, 2H), 3.67 (bt, 2H), 3.76 (bt, 2H) (ppm); $^{13}$C-NMR (CDCl$_3$): 61.75, 49.48, 44.97, 36.27, 35.26, 29.32 (ppm); IR (KBr) 3268, 2946, 2868, 1479, 1458, 1082, 1037, 1012 (cm$^{-1}$); Elementary analysis (C$_{12}$H$_{20}$O$_2$); Calcd.: C, 73.43; H, 10.27; Found: C, 73.18; H, 10.39

EXAMPLE 10

(i) Preparation of tricyclo[5. 2. 1. 0$^{2,6}$]decane-trans-3,5-dimethyl dicarboxylate A 500 ml, 4-necked flask equipped with a stirrer, thermometer, dropping funnel and nitrogen gas inlet tube was charged with 55.0 g (0.218 mole) of the tricyclo[5. 2. 1. 0$^{2,6}$]decane-cis-3,5-dimethyl dicarboxylate prepared in Example 9 (i), 300 ml of tetrahydrofuran and 4.80 g (0.043 mole) of potassium tert-butoxide. The mixture was stirred at 0° C. for 2 hours. With the addition of 20 ml of water, the reaction mixture was quenched and was concentrated to about 100 ml under reduced pressure. The concentrate was subjected to fractional extraction with 300 ml of water and 300 ml of ethyl acetate. The obtained organic layer was washed with water and concentrated under reduced pressure, giving 54 g of pale yellow solids. The solids were recrystallized from methanol, giving 49 g of white crystals having a melting point of 57° to 59° C. (yield 89%). It was confirmed by $^1$H-NMR, $^{13}$C-NMR, IR and elementary analysis that the crystals were identical with the contemplated tricyclo[5. 2. 1. 0$^{2,6}$]decane trans-3,5-dimethyl dicarboxylate.

(ii) Preparation of tricyclo[5. 2. 1. 0$^{2,6}$]decane-trans-3,5-dimethanol (alicyclic trans-diol of the formula (7) wherein n is 0)

A 300 ml autoclave equipped with an electromagnetic stirrer was charged with 30 g (0.12 mole) of the tricyclo[5. 2. 1. 0$^{2,6}$]decane-trans-3,5-dimethyl dicarboxylate prepared above in Example 10 (i), 150 ml of dioxane and 0.5 g of a copper-chromite catalyst. The system was fully replaced with hydrogen gas and was further supplied with hydrogen gas to a pressure of 200 kg/cm$^2$. Reduction was effected with stirring at 200° C. for 20 hours. After completion of the reaction, the system was cooled to 60° C. or lower, the catalyst was filtered off and the dioxane was distilled off under reduced pressure. The obtained pale yellow powder was recrystallized from a methanol-ethyl acetate solvent mixture, producing 18.5 g of white crystals with a melting point of 125° to 130° C. (yield 79%). It was confirmed by $^1$H NMR, $^{13}$C-NMR, IR and elementary analysis that the crystals were identical with the contemplated tricyclo[5. 2. 1. 0$^{2,6}$]decane-trans-3,5-dimethanol. The spectrum data are as follows.

$^1$H-NMR (CDCl$_3$): 0.75 (q, 1H), 0.91 (d, 1H), 0.98 (dd, 2H), 1.32 (d, 1H), 1.40–1.49 (m, 4H), 1.42 (s, 2H), 1.65–1.71 (m, 1H), 1.98 (s, 2H), 3.29–3.43 (m, 4H), 4.35 (t, 2H) (ppm); $^{13}$C-NMR (CDCl$_3$): 65.07, 51.29, 47.52, 39.53, 34.50, 32.82, 28.27 (ppm); IR (KBr): 3316, 2929, 2873, 1476, 1452, 1091, 1056, 1013 (cm$^{-1}$); Elementary analysis (cl$_2$H$_{20}$O$_2$); Calcd.: C, 73.43; H, 10.27; Found: C, 73.28; H, 10.33

EXAMPLE 11

Preparation of pentacyclo[6. 5. 1. 1$^{3,6}$. 0$^{2,7}$. 0$^{9,13}$] penta-decane-cis-10, 12-dimethanol (alicyclic cis-diol of the formula (6) wherein n is 1)

A 300 ml autoclave equipped with an electromagnetic stirrer was charged with 38.2 g (0.120 mole) of the pentacyclo[6. 5. 1. 1$^{3,16}$. 0$^{2,7}$. 0$^{9,13}$]pentadecane-cis-10, 12-dimethyl dicarboxylate prepared in Example 4, 150 ml of dioxane and 0.5 g of a copper-chromite catalyst. The system was fully replaced with hydrogen gas and was further supplied with hydrogen gas to a pressure of 200 kg/cm$^2$. Reduction was effected with stirring at 200° C. for 20 hours. After completion of the reaction, the system was cooled to 60° C. or lower, the catalyst was filtered off and the dioxane was distilled off under reduced pressure. The obtained pale yellow powder was recrystallized from hexane, producing 22.3 g of white crystals with a melting point of 73° to 77° C. (yield 71%). It was confirmed by $^1$H-NMR, $^{13}$C-NMR, IR and elementary analysis that the crystals were identical with the contemplated pentacyclo[6. 5. 1. 1$^{3,6}$ 0$^{2,7}$. 0$^{9,13}$] pentadecane-cis-10, 12-dimethanol. The spectrum data are as follows.

$^1$H-NMR (CDCl$_3$): 0.90–1.03 (m, 4H), 1.07 (d, 1H), 1.23 (d, 1H), 1.41–1.49 (m, 2H), 1.62 (s, 2H), 1.75–1.93 (m, 4H), 2.09 (bs, 2H), 2.25–2.38 (m, 2H), 2.25 (bs, 2H), 2.45 (d, 2H), 3.61 (dd, 2H), 3.71 (dd, 2H) (ppm); $^{13}$C-NMR (CDCl$_3$): 61.62, 50.12, 44.55, 43.51, 41.33, 39.69, 36.68, 35.79, 31.18 (ppm); IR (KBr): 3293, 2947, 2875, 1484, 1457, 1017, 903 (cm$^{-1}$); Elementary analysis (C$_{17}$H$_{26}$O$_2$); Calcd.: C, 77.82; H, 9.99; Found: C, 77.85; H, 10.11

EXAMPLE 12

Preparation of pentacyclo[6. 5. 1. 1$^{3,6}$. 0$^{2,7}$ 0$^{9,13}$] pentadecane-trans-10, 12-dimethanol (alicyclic trans-diol of the formula (7) wherein n is 1)

A 300 ml autoclave equipped with an electromagnetic stirrer was charged with 38.2 g (0.120 mole) of the pentacyclo[6. 5. 1. 1$^{3,6}$. 0$^{2,7}$·0$^{9,13}$]pentadecane-trans-10, 12-dimethyl dicarboxylate prepared in Example 5, 150 ml of dioxane and 0.5 g of a copper-chromite catalyst. The system was fully replaced with hydrogen gas and was further supplied with hydrogen gas to a pressure of 200 kg/cm$^2$. Reduction was effected with stirring at 200° C. for 20 hours. After completion of the reaction, the system was cooled to 60° C. or lower, the catalyst was filtered off and the dioxane was distilled off under reduced pressure. The obtained pale yellow powder was recrystallized from hexane, producing 23.5 g of white crystals with a melting point of 114° to 115° C. (yield 75%). It was confirmed by $^1$H-NMR, $^{13}$C-NMR, IR and elementary analysis that the crystals were identical with the contemplated pentacyclo[6. 5. 1. 1$^{3,6}$. 0$^{2,7}$. 0$^{9,13}$]pentadecane-trans-10, 12-dimethanol. The spectrum data are as follows.

$^1$H-NMR (CDCl$_3$): 0.83 (q, 1H), 0.91 (d, 1H), 0.98 (dd, 2H), 1.04 (d, 1H), 1.38 (d, 2H), 1.44 (d, 2H), 1.57 (d, 1H), 1.62–1.72 (m, 3H) 1.66 (bs, 2H), 1.84–1.93 (m, 3H), 2.10 (d, 4H), 3.52–3.68 (m, 4H) (ppm); $^{13}$C-NMR (CDCl$_3$): 67.18, 49.22, 47.77, 45.81, 45.29, 36.84, 36.46, 35.07, 34.17, 31.36 (ppm); IR (KBr): 3316, 2947, 2925, 2886, 2868, 1481, 1458, 1040, 903 (cm$^{-1}$); Elementary analysis (C$_7$H$_{26}$O$_2$); Calcd.: C, 77.82; H, 9.99; Found: C, 77.75; H, 10.08

What we claim is:

1. A process for preparing an alicyclic cis-dicarboxylic acid represented by the formula

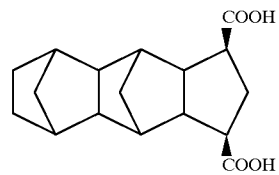

(2)

the process comprising subjecting to oxidative cleavage reaction the double bond of an alicyclic monoolefin represented by the formula

(8)

wherein n is 1.

2. The process according to claim 1 wherein the oxidative cleavage reaction is conducted under acidic conditions using a permanganate as an oxidizing agent.

3. A process for preparing an alicyclic trans-dicarboxylic acid represented by the formula

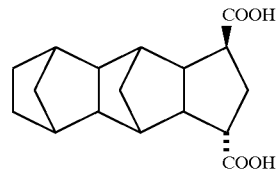

(3)

the process comprising the steps of:

esterifying the alicyclic cis-dicarboxylic acid recited in claim 1: isomerizing the resulting alicyclic cis-dicarboxylic diester

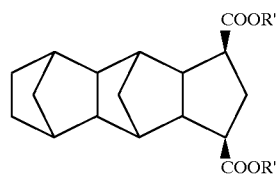

(4)

into a trans form; and hydrolyzing the trans form.

4. The process according to claim 3 wherein the isomerization is effected using a metal alkoxide as a catalyst.

5. A process for preparing an alicyclic cis-dicarboxylic diester represented by the formula

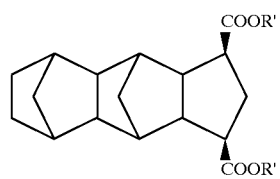

(4)

wherein R' is a low alkyl group having 1 to 4 carbon atoms, the process comprising

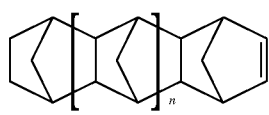
(8)

esterifying the alicyclic cis-dicarboxylic acid recited in claim 8.

6. A process for preparing an alicyclic trans-dicarboxylic diester represented by the formula

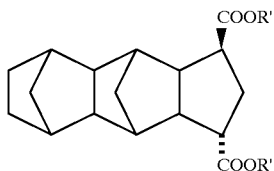
(5)

wherein R' is a lower alkyl group having 1 to 4 carbon atoms, the process comprising isomerizing the alicyclic cis-dicarboxylic diester recited in claim 5

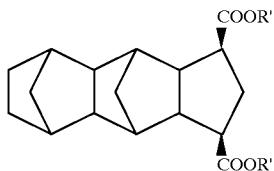
(4)

into a trans form.

7. The process according to claim 6 wherein the isomerization is effected using a metal alkoxide as a catalyst.

8. A process for preparing an alicyclic cis-diol represented by the formula

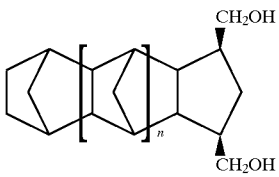
(6)

wherein n is 1, the process comprising

(8)

reducing the cis-dicarboxylic diester recited in claim 5.

9. The process according to claim 8 where the reduction reaction is effected through catalytic hydrogenation in the presence of a hydrogenation catalyst.

10. A process for preparing an alicyclic trans-diol represented by the formula

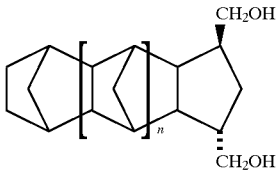
(7)

wherein n is 1, the process comprising the steps of;

(8)

isomerizing the cis-dicarboxylic diester recited in claim 5 into a trans form; and reducing the trans form.

11. The process according to claim 10 where the isomerization reaction is effected in the presence of a metal alkoxide as a catalyst, and the reduction reaction is effected through catalytic hydrogenation in the presence of a hydrogenation catalyst.

12. A process for preparing an alicyclic cis-diol represented by the formula

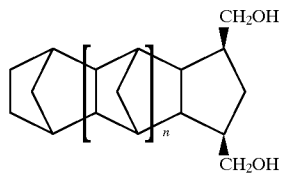
(6)

where n is 0, said process comprising the steps of:

cleaving by oxidation the double bond of an alicyclic monoolefin represented by the formula

(8)

wherein n is 0, to give a cis-dicarboxylic acid;

esterifying said acid into a cis-dicarboxylic diester; and reducing said diester.

13. The process according to claim 12, where the oxidative cleavage reaction is conducted under acidic conditions using a permanganate as an oxidizing agent and the reduction reaction is effected through catalytic hydrogenation in the presence of a hydrogenation catalyst.

14. A process for preparing an alicyclic trans-diol represented by the formula

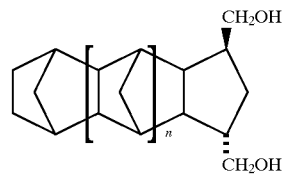
(7)

wherein n is 0, the process comprising;

cleaving by oxidation the double bond of an alicyclic monoolefin represented by the formula

(8)

where n is 0, to give a cis-dicarbxylic acid;

esterifying said acid into a cis-dicarboxylic diester;

isomerizing said diester into a trans form; and reducing said trans form.

15. The process according to claim 14, where the oxidative cleavage reaction is conducted under acidic conditions using a permanganate as an oxidizing agent, the isomerization reaction is effected in the presence of a metal alkoxide as a catalyst, and the reduction reaction is effected through catalytic hydrogenation in the presence of a hydrogenation catalyst.

* * * * *